(12) United States Patent
Esquivel-Upshaw et al.

(10) Patent No.: US 10,813,847 B2
(45) Date of Patent: Oct. 27, 2020

(54) DIELECTRIC COATINGS FOR FIXED AND REMOVABLE ORAL PROSTHETIC RESTORATIONS

(71) Applicant: University of Florida Research Foundation, Inc., Gainesville, FL (US)

(72) Inventors: Josephine F. Esquivel-Upshaw, Gainesville, FL (US); Fan Ren, Gainesville, FL (US); Arthur E. Clark, Newberry, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 15/772,345

(22) PCT Filed: Oct. 28, 2016

(86) PCT No.: PCT/US2016/059343
§ 371 (c)(1),
(2) Date: Apr. 30, 2018

(87) PCT Pub. No.: WO2017/075364
PCT Pub. Date: May 4, 2017

(65) Prior Publication Data
US 2018/0325780 A1    Nov. 15, 2018

Related U.S. Application Data

(60) Provisional application No. 62/304,654, filed on Mar. 7, 2016, provisional application No. 62/248,988, filed on Oct. 30, 2015.

(51) Int. Cl.
*B32B 9/00*     (2006.01)
*A61K 6/20*     (2020.01)
(Continued)

(52) U.S. Cl.
CPC ............... *A61K 6/20* (2020.01); *A61K 6/833* (2020.01); *A61C 13/08* (2013.01); *A61K 6/818* (2020.01); *C23C 4/11* (2016.01)

(58) Field of Classification Search
None
See application file for complete search history.

(56) References Cited

U.S. PATENT DOCUMENTS

| 4,828,117 A | 5/1989 | Panzera et al. |
| 5,104,319 A | 4/1992 | Evans et al. |

(Continued)

FOREIGN PATENT DOCUMENTS

| JP | 4945743 | 3/2012 |
| RU | 2013127770 A | * 12/2014 |

(Continued)

OTHER PUBLICATIONS

International Search Report for PCT/US2016/059343 dated Feb. 16, 2017.

(Continued)

*Primary Examiner* — Seth Dumbris
*Assistant Examiner* — Kim S. Horger
(74) *Attorney, Agent, or Firm* — Thomas I Horstemeyer, LLP

(57) ABSTRACT

Dental prosthetic restoration coatings made of dielectric materials, methods of fabricating the same, as well as methods of testing dental prosthetic restorations are provided. A prosthetic restoration coating can include dielectric materials such as $Al_2O_3$, $ZrO_2$, $SiN_x$, SiC, and $SiO_2$. Application can take place using plasma enhanced chemical vapor deposition (PECVD) methods, and alternating materials can be used to achieve desired anticorrosive, structural integrity, hardness, adhesion, and color characteristics. A testing method can include immersing a test device in solutions of (Continued)

differing pH, with or without abrasive steps. The cycling can include an acidic solution and a basic solution, with an optional neutral solution. As the abrasive step, a chewing simulator can be utilized.

9 Claims, 13 Drawing Sheets

(51) Int. Cl.
    *A61K 6/833*     (2020.01)
    *A61K 6/818*     (2020.01)
    *C23C 4/11*     (2016.01)
    *A61C 13/08*     (2006.01)

(56) References Cited

U.S. PATENT DOCUMENTS

| | | | |
|---|---|---|---|
| 7,022,173 B2 * | 4/2006 | Cummings | C04B 35/50 106/35 |
| 8,591,994 B2 | 11/2013 | Deisenroth et al. | |
| 2005/0127544 A1 * | 6/2005 | Brodkin | A61K 6/807 264/16 |
| 2007/0003908 A1 | 1/2007 | Porter | |
| 2008/0044451 A1 * | 2/2008 | Steinmuller-Nethl | A61L 27/303 424/423 |
| 2009/0215010 A1 | 8/2009 | Tagami et al. | |
| 2011/0318714 A1 * | 12/2011 | Nikawa | A61L 27/303 433/222.1 |
| 2013/0236854 A1 * | 9/2013 | McEntire | A61C 8/0013 433/173 |
| 2015/0359613 A1 * | 12/2015 | Brodbeck | A61K 6/024 433/173 |

FOREIGN PATENT DOCUMENTS

| | | | | |
|---|---|---|---|---|
| WO | 2012027091 A1 | 3/2012 | | |
| WO | WO-2014122189 A1 * | 8/2014 | | A61C 8/0013 |
| WO | WO-2014173541 A1 * | 10/2014 | | A61C 8/0013 |

OTHER PUBLICATIONS

International Search Report and Written Opinion for PCT/US2019/044556 dated Oct. 22, 2019.

* cited by examiner

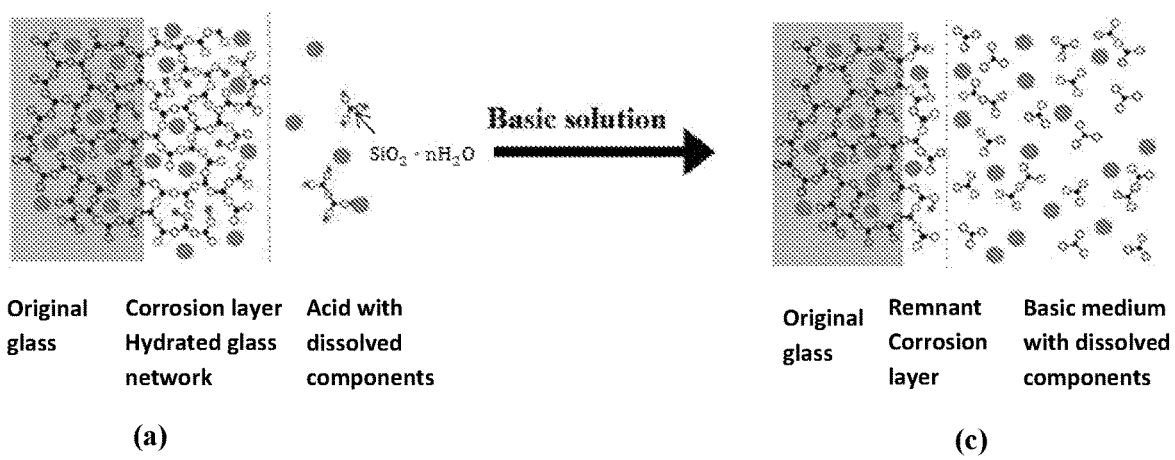
FIG. 5A
FIG. 5C
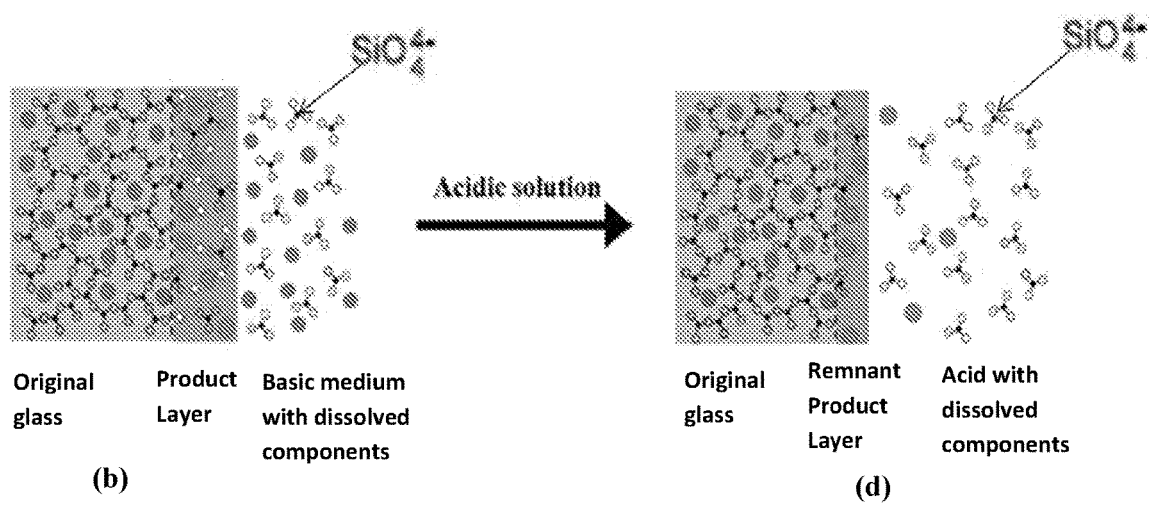
FIG. 5B
FIG. 5D

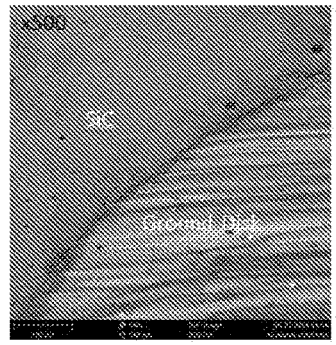
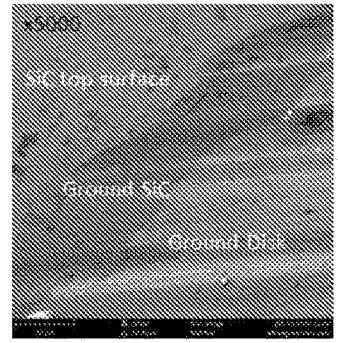
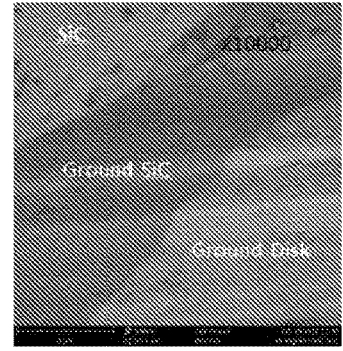
FIG. 13A　　　　　　FIG. 13B　　　　　　FIG. 13C
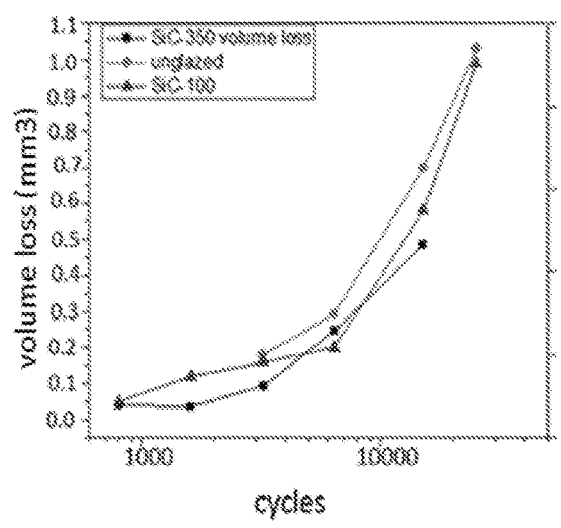
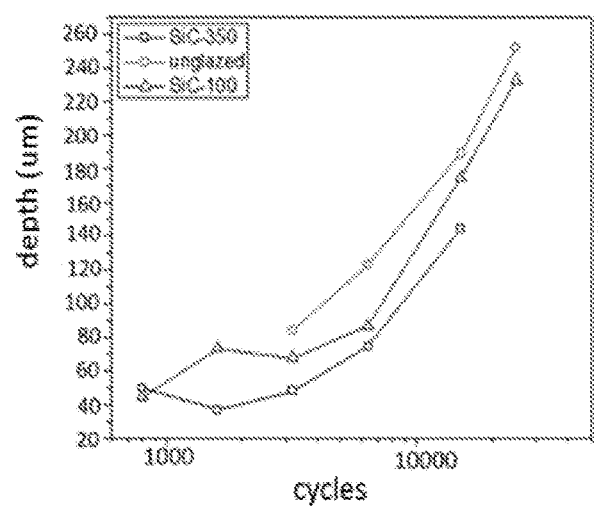
FIG. 14A　　　　　　　　　　　　FIG. 14B

DIELECTRIC COATINGS FOR FIXED AND REMOVABLE ORAL PROSTHETIC RESTORATIONS

CROSS REFERENCE TO RELATED APPLICATIONS

This application is the 35 U.S.C. § 371 national stage application of PCT Application No. PCT/US2016/059343, filed Oct. 28, 2016, where the PCT claims the benefit of U.S. Provisional Application Ser. No. 62/248,988, filed Oct. 30, 2015, and U.S. Provisional Application Ser. No. 62/304,654, filed Mar. 7, 2016, the disclosures of which are all hereby incorporated by reference in their entireties, including any figures, tables, and drawings.

BACKGROUND OF THE INVENTION

Prosthetic restorations of the oral cavity can be fixed or removable. Examples of fixed restorations include crowns, bridges, inlays, partials and onlays, while examples of removable restorations include dentures and partials. Materials for prosthetic restorations range from completely metallic, to metal substructures veneered with glass-ceramics, to all-ceramic materials. Over the past 40 years, ceramics have become the primary materials for fixed dental prostheses (FDPs) to replace missing teeth. However, the physical property limitations of ceramics restrict their use for certain conditions and account for a significantly greater percentage of technical complications and lower success rates compared with all-metal or metal-ceramic prostheses.

The weak link of ceramic restorations is the glass-based veneering ceramic, which has low fracture strength and low fracture toughness. Due to the corrosive environment present in the oral cavity, clinical studies have revealed the survival rate for ceramic-ceramic fixed dental prostheses is as low as 76.5% over a period of four years. Even metal-ceramic fixed dental prostheses showed only a 92% survival rate for an observation period of 10 years.

The high failure rate of prosthetic restorations is due to their materials having to perform in a constantly aqueous environment with drastic changes in temperature and pH, depending on what the user is eating or drinking. In addition, there are also a myriad of oral microbiota that exist within the oral cavity and can colonize the surfaces of prosthetic restorations. These bacteria can also affect the pH within the oral cavity and the surface of the restoration, cause surface roughness, and create further places for bacteria to colonize.

Another shortfall in current dental technology is the inability to properly emulate the oral environment. For instance, ISO standard 6872 for dental ceramics only requires evidence of minimal chemical solubility for dental ceramic materials when exposed to a 4% HAc solution. In actuality, ceramics undergo surface degradation and corrosion through a complex mechanism, which involves the breakdown of the glass phase and release of component ions from the microstructure. This breakdown is influenced by several factors, which include mechanical abrasion and a concurrent loss of ions as a result of chemical interactions with the environment.

BRIEF SUMMARY

To address the above-mentioned problems, new materials and methods to form the surface of dental prosthetic restorations are needed, as well as methods for effectively testing dental prosthetic restorations. The subject invention provides novel and advantageous dental prosthetic restoration coatings, methods of forming the same, and methods of using the same, as well as methods of testing dental prosthetic restorations.

In one embodiment, a dental prosthetic restoration includes a first dielectric coating. A second dielectric coating may additionally be formed. Multiple layers of coatings may be formed to achieve the desired surface, wear, chemical resistance, and color characteristics. For example, two or more dielectric layers can be alternately arranged for a total of, e.g., 2 to 20 layers. Sample dielectric materials that can be used as coatings include $Al_2O_3$, $ZrO_2$, $SiN_x$, SiC, and $SiO_2$. The thickness of each layer can range from, for example, 5 nanometers (nm) to 100 μm and be applied using, for example, a PECVD method, though embodiments are not limited thereto.

In another embodiment, a method for testing dental prosthetic restorations includes providing a basic solution, providing an acidic solution, immersing a test device in the basic solution or the acidic solution, and evaluating corrosion and damage of the test device. The method may further include providing a neutral solution and immersing the test device in the neutral solution. The basic solution may have a pH of, for example, 9.5 to 10.5, the acidic solution may have a pH of, for example, 1.5 to 2.5, and the neutral solution may have a pH of, for example, 6.5 to 7.5, though embodiments are not limited thereto. The test device may be cycled between the different solutions (e.g., acid, base, or neutral) for different amounts of time (e.g., hours, days, weeks, or months). Additionally, an abrasive step or steps can be added, such as the use of a chewing simulator.

BRIEF DESCRIPTION OF THE DRAWINGS

FIG. 5A to 5D are schematic illustrations of the pH cycling phenomenon and the rationale for why there is greater surface degradation in cycling immersion versus constant immersion.

FIGS. 13A to 13C are SEM micrographs showing the bond between a substrate and an SiC coating, according to an embodiment of the present invention.

FIG. 14A is a graph of volume loss versus simulated chewing cycles in an experimental test of an embodiment of the present invention.

FIGS. 14A and 14B are graphs of depth versus simulated chewing cycles in an experimental test of an embodiment of the present invention.

DETAILED DESCRIPTION

Figure 1A:
FIG. 1A shows an image of a lower first molar with excessive roughening of buccal cusps (lower left) after one year.
Figure 1B:
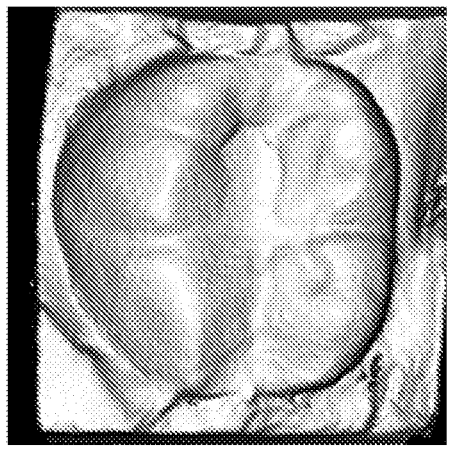
FIG. 1B is a laser scanned image of the molar of FIG. 1A at cementation.
Figure 1C:
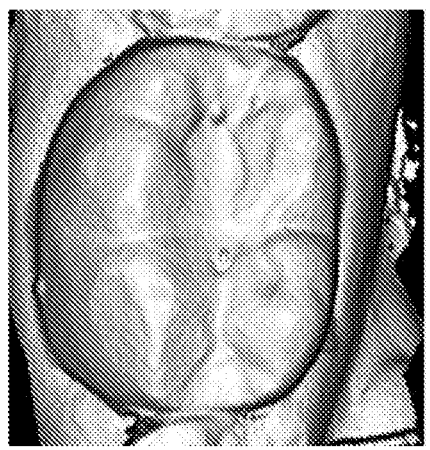
FIG. 1C is laser scanned image of the molar of FIG. 1A at year 2 with noticeable wear on buccal surfaces.
Figure 1D:
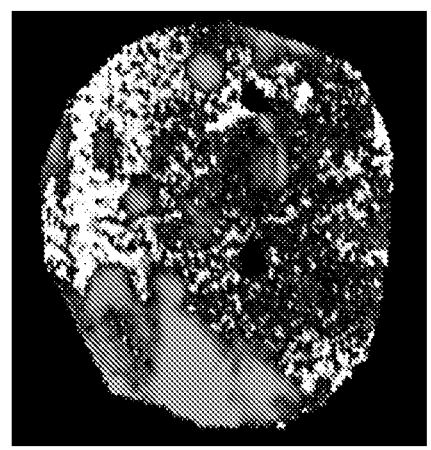
FIG. 1D is a laser-scanned image with red showing the location of maximum wear areas.

The subject invention provides novel and advantageous dental prosthetic restoration coatings, methods of forming the same, and methods of using the same, as well as methods of testing dental prosthetic restorations. A dental prosthetic restoration can include a first dielectric coating. A second dielectric coating can additionally be included. A third dielectric coating can be added. In certain embodiments, multiple layers of coatings can be included to achieve desired surface, wear, chemical resistance, and/or color characteristics. For example, two dielectric layers can be alternately arranged for a total of, e.g., 2 to 100 layers (including every integer in between; i.e. 2, 3, 4, 5 . . . 99, 100). More specifically, two or more dielectric layers can be alternately arranged for a total of 4 to 40 layers. Further two, three, four, five, six, seven, eight, nine, and ten or more layers of the same coating can be applied. The material of the first, the second (if present), and each subsequent (if present) dielectric coating can be, for example, $Al_2O_3$, $ZrO_2$, $SiN_x$, SiC, $SiO_2$, or a combination thereof, though embodiments are not necessarily limited thereto. The thickness of each layer can range from, for example, 5 nanometers (nm) to 10,000 nm. More specifically, the thickness of each layer can range from 5 nm to 500 nm. The thickness of each layer can be, for example, any of the following values, about any of the following values, at least any of the following values, at least about any of the following values, not more than any of the following values, not more than about any of the following values, or within any range having any of the following values as endpoints (with or without "about" in front of one or both of the endpoints), though embodiments are not limited thereto: 5 nm, 10 nm, 15 nm, 20 nm, 25 nm, 30 nm, 40 nm, 50 nm, 60 nm, 70 nm, 80 nm 90 nm, 100 nm, 150 nm, 200 nm, 250 nm, 300 nm, 350 nm, 400 nm, 450 nm, 500 nm, 600 nm, 700 nm, 800 nm, 900 nm 1000 nm, 2000 nm, 3000 nm, 4000 nm, 5000 nm, and 10000 nm. Each layer can be applied using, for example, a plasma-enhanced chemical vapor deposition (PECVD) method, a sputtering system, or a plasma spray method, although embodiments are not limited thereto.

A method for testing dental prosthetic restorations according to an embodiment of the present invention can include providing a basic solution, providing an acidic solution, immersing a test device in the basic solution and/or the acidic solution, and evaluating corrosion and damage of the test device. Evaluating the corrosion and damage of the dental prosthetic restoration (or test device) can be done by analyzing the dental prosthetic restoration directly (e.g., using microscopy or surface elemental analysis) or collecting testing solution samples and analyzing the test solutions to determine the content and concentration of solutes present. The method can further include providing a neutral solution and immersing the test device in the neutral solution. The basic solution can have a pH of, for example, 8.0 to 14.0 (more specifically, 9.5 to 10.5), the acidic solution can have a pH of, for example, 0.5 to 6.0 (more specifically, 1.5 to 2.5), and the neutral solution can have a pH of, for example, 6.1 to 7.9 (more specifically, 6.5 to 7.5), though embodiments are not limited thereto. The test device can be cycled among the different solutions in any order (e.g., acid, base, neutral, or base, acid, neutral, etc.) for different amounts of time (e.g., hours, days, weeks, or months). Each cycle can repeat the same order of solutions, or the order of solutions can be changed from cycle to cycle. Additionally, one or more abrasive steps can be added, such as the use of a chewing simulator, at any stage of the testing (e.g., between cycles, after a certain number of cycles, with each cycle, within every other cycle, within every third cycle, etc.).

There are multiple options for producing the acidic, basic, and neutral solutions. A buffer solution can be formed to keep pH levels constant. Examples of acidic solutions include hydrochloric acid and potassium chloride (pH=2); citric acid, hydrochloric acid, and sodium chloride (pH=3); citric acid, sodium hydroxide, and sodium chloride (pH=3); and potassium hydrogen phthalate and formaldehyde (pH=3). One option for a neutral solution (i.e., pH=7) is sodium hydroxide with potassium dihydrogen phosphate. Examples of basic solutions include glycine and sodium hydroxide, sodium carbonate and sodium hydroxide, sodium tetraborate and sodium hydroxide, and sodium bicarbonate and sodium hydroxide (pH=10).

Figure 2A:
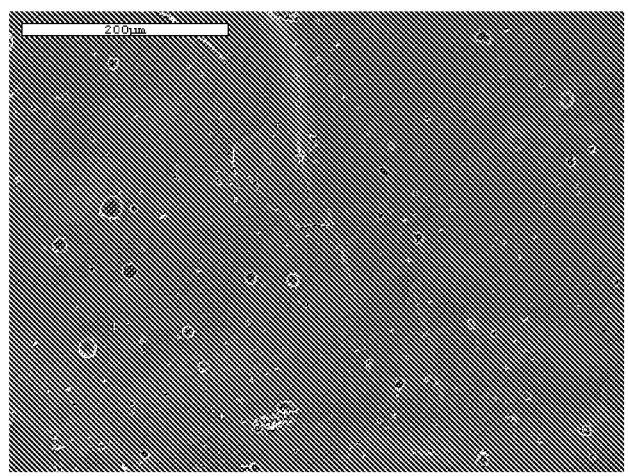
FIGS. 2A to 2C are scanning electron microscope (SEM) images of a glass ceramic veneer after: (A) 0 days; (B) pH 2, 30 days; and (C) pH 10, 30 days.
Figure 2B:
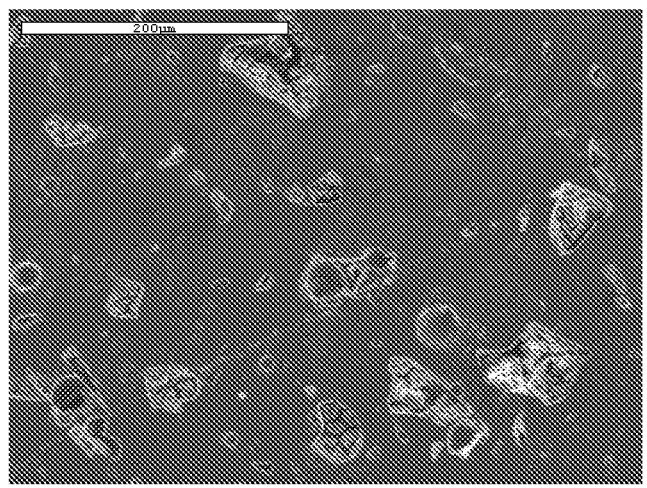
Figure 2C:
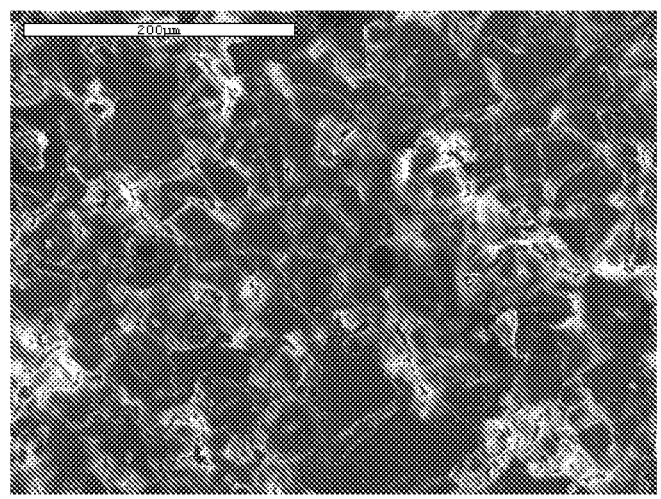
Figure 3A:
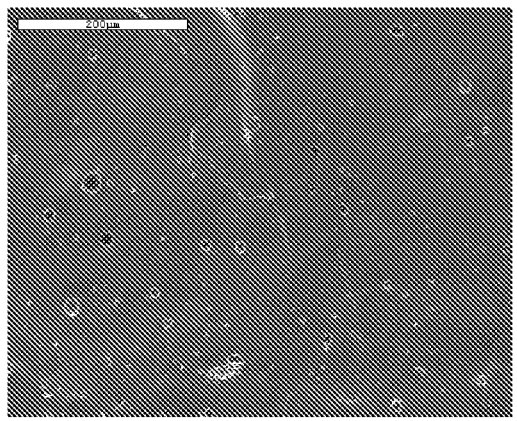
FIG. 3A to 3D are SEM images of pH cycled surfaces with: (A) no exposure; (B) pH 2, 7, 10; (C) pH 7, 10, 2; and (D) pH 10, 2, 7.
Figure 3B:
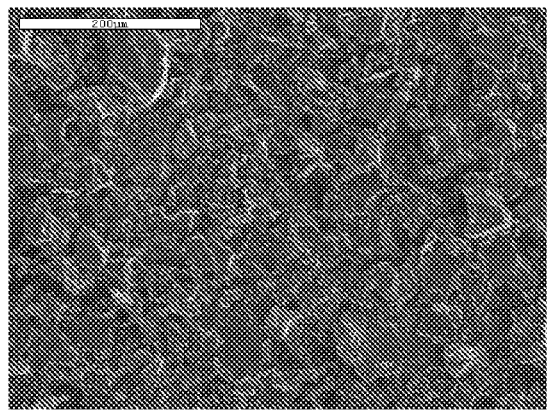
Figure 3C:
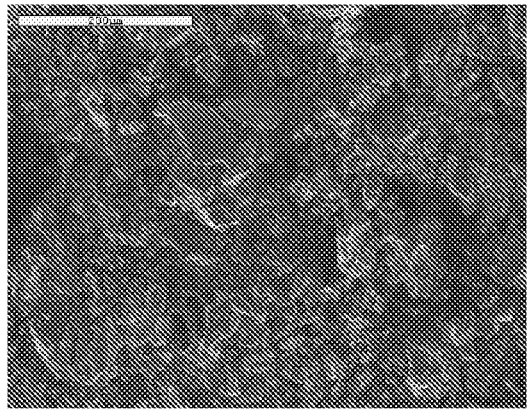
Figure 3D:
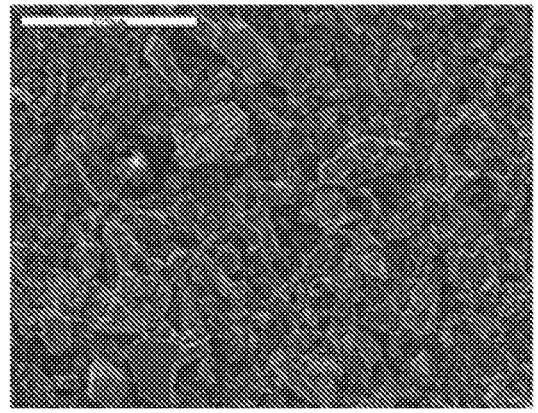

FIGS. 1A to 1D show images of ceramic materials from patients that reported significant roughening of crown surfaces (Esquivel-Upshaw, Dieng, Clark, Neal and Anusavice, 2013; Esquivel-Upshaw, 2012, which is hereby incorporated by reference in its entirety). Referring to FIGS. 1A to 1D, there is a significant difference in ion concentrations of veneering ceramics as a function of the veneer type (composition), solution pH, and duration of exposure. This suggests that at a higher pH there is a substantial release of silicon (Si) over time, leading to a total breakdown of the glass phase, as evidenced by scanning electron microscopy (SEM) analysis shown in FIGS. 2A and 2C. At a lower pH the data suggests that there is a release of ions that simulates an ionic exchange mechanism (FIGS. 2A and 2B).

Analysis can be performed to determine the effect of pH cycling on the surface degradation of ceramics. This is a more representative simulation of the oral environment in which the pH fluctuates from one pH buffer solution to another. Results suggest that there is a tendency for greater ion release, and thus for greater surface degradation, during pH cycling than for exposure to a constant pH environment. SEM analysis of the surface reveals that severe breakdown occurs within the surface of all three groups exposed to the pH cycling process (FIG. 3) compared with the unexposed baseline group. A comparison between the SEM images of discs exposed to a constant pH buffer solution revealed greater surface damage for all of the surfaces subjected to the pH cycling process.

Furthermore, ion release data showed a marked difference between related corrosion testing methods involving constant immersion in an acidic environment versus the cycling pH methodology disclosed herein. These new testing methods, including alternating low and high pH solutions, provide superior corrosion testing because of the different mechanisms involved and the more stringent standards placed on dental materials.

The pH cycling phenomenon can be explained, at least in part, by the mechanism of glass corrosion. The models illustrated in FIGS. 5A and 5B help describe the glass corrosion mechanism in acidic or basic solutions (see also, e.g., Hermann, 2013, which is hereby incorporated by reference in its entirety). Referring to FIG. 5A, a corrosion layer with a hydrated glass network is formed in acidic environments by leaching the network modifiers, with a minimal amount of $SiO_2$ $(H_2O)_n$ molecules in the aqueous solution. The leaching process of network modifiers and the formation of a hydrated glass network has the following reaction:

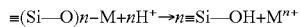
$\equiv(Si-O)n-M+nH^+ \rightarrow n\equiv Si-OH+M^{n+}$

While the dissolution of the hydrated network reaction is shown as:

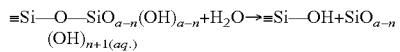
$\equiv Si-O-SiO_{a-n}(OH)_{a-n}+H_2O \rightarrow \equiv Si-OH+SiO_{a-n}(OH)_{n+1(aq.)}$ The dissolution of the hydrated network is the rate-limiting process. This explains why only a very small amount of Si ions are released for a glass ceramic veneer immersed in a constant low pH solution (e.g., pH 2 solution with 0.128 mg/g for 3-day and 0.792 mg/g for 30 day constant immersion; see also Example 1). However, in a basic environment, the glass network dissolves as shown in FIG. 5B, and the dissolution process is as follows:

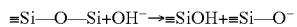
$\equiv Si-O-Si+OH^- \rightarrow \equiv SiOH+\equiv Si-O^-$

The network modifiers are more stable in the base solution, and a layer of these network modifiers along with fragments of $SiO_4^{4-}$ form on the glass surface. Constant immersion in pH 10 (see Example 1) demonstrated Si concentrations of 2.41 mg/g for 3 days and 24.1 mg/g for 30 days.

As a result of the cycling process, a completely different reaction occurs as shown in FIGS. 5C and 5D. As discussed herein, a hydrated glass network forms after the ceramic is immersed in the acidic solution. Referring to FIG. 5C, this hydrated glass network can be easily dissolved in the basic solution. This accounts for the very high Si concentration (20 times larger) detected every time the cycling sequence cycled to pH 10, regardless of the sequence pattern (i.e. 2, 7, 10 or 10, 2, 7); see also Example 1. When the glass-ceramic immersed in the basic solution is exposed to acidic solution, the acid easily dissolves the network modifier layer. The fragments of $SiO_4^{4-}$ trapped in the network modifier layer are then released to the acidic solution. This accounts for the much higher Si concentration detected in the low pH solution (e.g., pH 2 solution) during cycling (see also, Example 1—the amount of Si released at a constant pH 2 for 30 days was 0.792 mg/g solution; this value is much less than the Si released during cycling sequence 10, 2, 7 at the second cycle of pH 2 (1.05 mg/g)).

Embodiments of the subject invention include methods of testing corrosion and/or failure resistance of dental prostheses by immersion in solutions having different pH. The methods of testing can be applied to all (including fixed, removable, acrylic-based, and ceramic-based) dental prostheses, as well as materials and devices that are not intended for direct dental use (e.g., a fluorapatite disk with a dielectric coating that mimics a dental prosthetic for testing). Although certain acidic (pH 2), neutral (pH 7), and basic (pH 10) pH values are disclosed in the examples herein, many different basic and/or acidic solutions can be used that each have different pHs. Additionally, the duration for a cycle can be any reasonable amount of time (e.g., seconds, minutes, hours, days, weeks, or even months), and the duration does not have to be the same for each submersion. The duration for each cycle can be, for example, any of the following values, about any of the following values, at least any of the following values, at least about any of the following values, not more than any of the following values, not more than about any of the following values, or within any range having any of the following values as endpoints (with or without "about" in front of one or both of the endpoints), though embodiments are not limited thereto: 5 seconds, 10 seconds, 20 seconds, 30 seconds, 1 minute, 2 minutes, 5 minutes, 10 minutes, 20 minutes, 30 minutes, 1 hour, 2 hours, 3 hours, 4 hours, 5 hours, 6 hours, 9 hours, 12 hours, 18 hours, 1 day, 2 days, 3 days, 1 week, 2 weeks, 1 month, 2 month, or three months. Each submersion can be at the same or different temperatures (e.g., from 0° C. to 120° C.). For example, average body temperature can be applied (i.e. 37° C.) or elevated temperatures (e.g., 50° C.) can be used to accelerate corrosion. The temperature for each cycle can be, for example, any of the following values, about any of the following values, at least any of the following values, at least about any of the following values, not more than any of the following values, not more than about any of the following values, or within any range having any of the following values as endpoints (with or without "about" in front of one or both of the endpoints), though embodiments are not limited thereto (all numerical values are in ° C.): 15, 20, 25, 30, 35, 37, 40 45, 50, 60, 80, or 100. In addition, an abrasive step or steps (e.g., a chewing simulator) can be inserted before, between, or during each (or some) immersion step(s).

FDPs can range in price from $500-$10,000, depending on the materials used, the expertise of the dentist, and the number of units involved. As part of the $50 billion spent annually by Americans on dental care, there is an expectation that these restorations: (1) will last for several years; (2) will not cause undue harm; and (3) will not compromise overall oral health. One type of prosthetic rehabilitation is removable restorations, which includes complete dentures and partial dentures. These are generally constructed from an acrylic resin material and a base noble metal. The resin material can be composed of fibers interspersed within a polymethylmethacrylate material.

Figure 6:
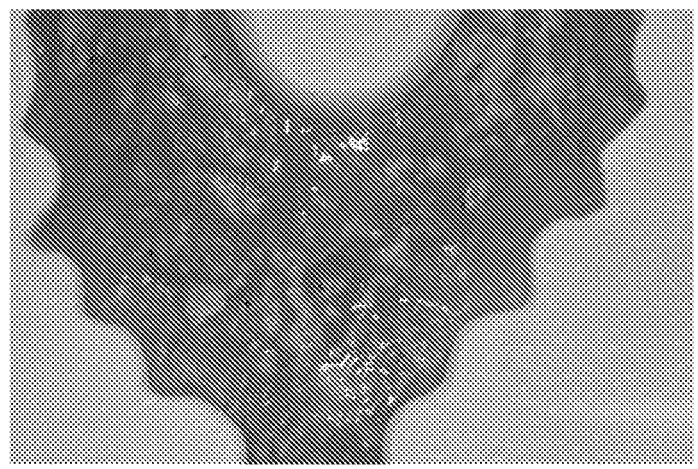
FIG. 6 illustrates the tissue surface of a removable partial denture colonized with bacteria resulting from poor oral hygiene and surface roughness.
Figure 7:
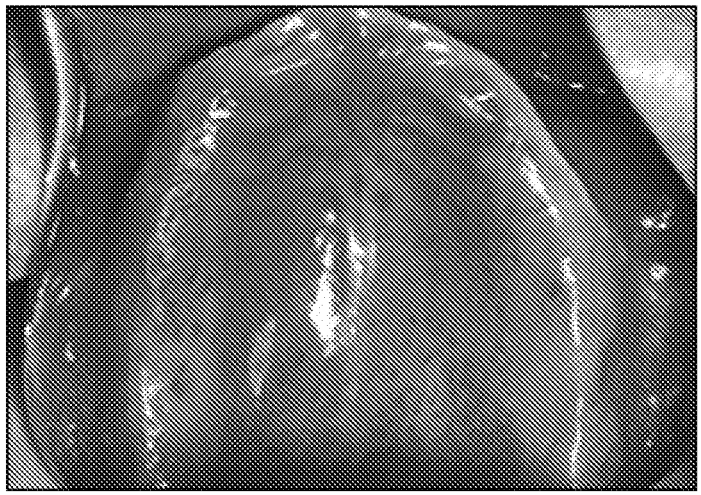
FIG. 7 is an image of an edentulous maxilla showing severe inflammation as a result of contact with bacterial colonies on the denture.

Bacterial adhesion to a substrate is a multifactorial process that involves surface properties inherent to both the bacteria and the biomaterial. The initial phase of bacterial colonization involves the formation of a biofilm on the surface of a material. Acrylic and resin materials are both hydrophobic and possess surface roughness, which is conducive to biofilm formation. Material processing leads to numerous pores within the substrate, which can account for the inherent surface roughness. This leads to oral flora colonizing the surface and causing oral and systemic infections in the individual. FIG. 6 shows the undersurface of a removable prosthesis. The surface is littered with bacterial colonies as a result of poor oral hygiene and the conducive nature of the acrylic material to bacterial colonization. FIG. 7 shows an edentulous maxilla that is highly inflamed as a result of bacteria proliferating on the tissue surface of the denture. The coatings of the subject invention, which can include, e.g., silicon carbide, can provide a smooth surface as evidenced by SEM and also increase the surface contact angle, minimizing biofilm formation and surface colonization.

Embodiments of the subject invention include surface coatings that can be applied to both fixed and permanent dental prostheses. These coated ceramic restorations are esthetic and have a significantly higher survival rate than those produced from current ceramic systems. In addition, the surface coating can result in improved quality of life of the dental population by reducing the need for prosthesis replacements.

Table 1 shows mechanical and chemical properties of different dielectric materials of the subject invention. $Al_2O_3$ demonstrates good mechanical properties, but poor resistance to corrosion in both low and high pH solutions. $ZrO_2$ demonstrates good chemical durability, but its abrasive hardness is not as good as some other dielectric materials. $SiN_x$ demonstrates good mechanical properties with reasonable chemical durability. Among all the materials listed in Table 1, SiC can be the most effective material for a veneer coating. SiC demonstrates high abrasive hardness, as well as excellent chemical resistance in both acidic and basic solutions. In addition, a fast deposition rate can be achieved with SiC, which is important in establishing a thorough and high output coating process.

As there is a difference in refractive indices between the dielectric coating layer and glass-ceramic veneers, a single layer of dielectric material coated on the veneer can alter the color of the veneer. Multiple layers of two dielectric films with different refractive indices can be used as reflective facet mirror coatings. The larger the difference in the refractive indices between these two dielectrics, the easier it is to adjust the color of the composite dielectric film. Although both the mechanical and chemical resistive properties of $SiO_2$ are not as good as other dielectrics, it is the best candidate for color adjustment of the dielectric coating, and therefore the best candidate to be used with SiC as part of the multiple layer composite. Furthermore, $SiO_2$ deposited on glass-based veneers should form the most stable and complete bonds as compared to other dielectrics.

TABLE 1

Mechanical and chemical properties of several dielectric coating materials

|  | $Al_2O_3$ | $ZrO_2$ | $SiN_x$ | SiC | $SiO_2$ |
|---|---|---|---|---|---|
| Refractive Index | 1.76 | 2.15 | 1.93 | 2.1-2.5 | 1.45 |
| Hardness (Kg/mm$^2$) | 2011 | 1160 | 1580 | 2800 | 820 |
| Abrasive Hardness (Mohs) | 9 | 6.5 | 9 | 9-10 | 6-7 |
| PECVD Deposition Rate (nm/min) | 6.8 | 9 | 7 | 20-125 | 40 |
| Flexural Strength (MPa) | 330 | 900 | 830 | 550 | 150 |
| Etch rate in 10:1 $H_2O$:HF (nm/min) | 160 | 1.7 | 1.1 | no etch | 23 |
| Etch rate in KOH 30 wt. % (nm/min) | 80 | no etch | 0.07 | no etch | 1.5 |

Figure 8A:
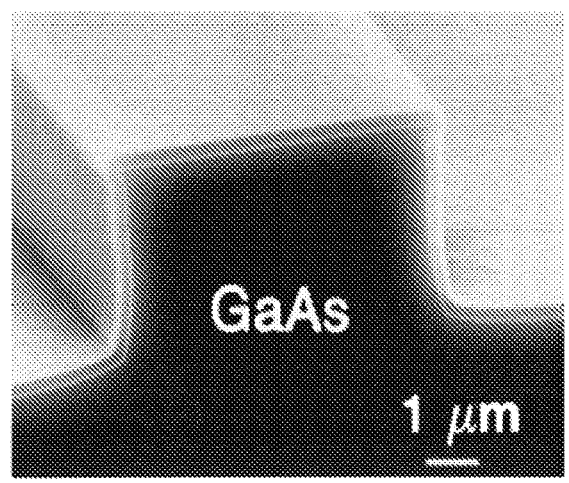
FIG. 8A is an SEM photograph of a ridge mesa formed on a gallium arsenic substrate conformably covered with 400 nm PECVD $SiO_2$.
Figure 8B:
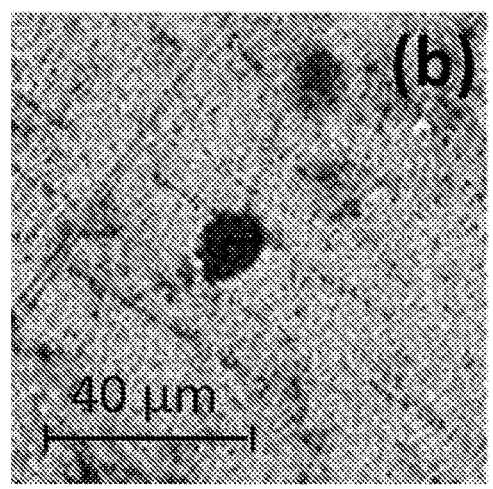
FIG. 8B is an SEM photograph displaying scratches and pores on the surface of a fluorapatite disk.
Figure 8C:
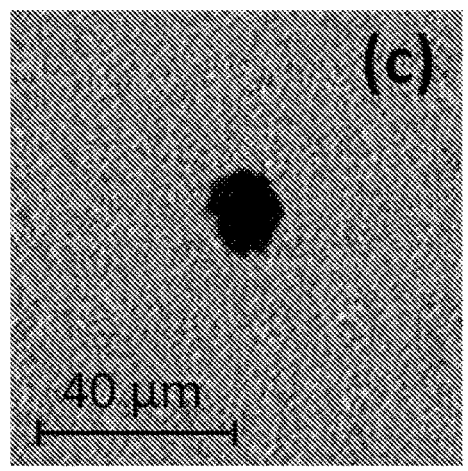
FIG. 8C is an SEM photograph of a fluorapatite disk surface that has been planarized using a silicon carbide (SiC) film.

Plasma enhanced chemical vapor deposition (PECVD) can be used to deposit high quality dielectrics at relatively low temperatures (e.g., 250-350° C.). The low temperature process is critical for coating ceramic prostheses and acrylic based resin materials without them being damaged. Other advantages of the PECVD process are good step coverage and fast deposition rates. Referring to FIG. 8A, 400 nm of $SiO_2$ was conformably deposited over a rectangular ridge fabricated on a gallium arsenic substrate using a reactive plasma etching system. The thickness of the $SiO_2$ layer is identical on the bottom, the top, and the edge of the etched ridge due to a long free mean path of the reactive ions under vacuum deposition. This capability is important for completely coating irregular shapes of ceramic prostheses and acrylic dentures. Being able to deposit 250 nm PECVD SiC on a fluorapatite disk also shows the capability of planarization. Referring to FIG. 8B, the surface of the fluorapatite disks were full of scratches and pores. The SiC film was able to planarize the scratches on the fluorapatite surface, as shown in FIG. 8C.

In an embodiment, silicon dioxide ($SiO_2$), silicon nitride, and/or silicon carbide can be deposited using radiofrequency, plasma-enhanced chemical vapor deposition (rf PECVD) in a Plasma Therm 790 load-luck system. Nitrous oxide ($N_2O$)/2% silane ($SiH_4$) balanced in argon, 5% ammonia balanced in argon/$SiH_4$, and methane ($CH_4$)/$SiH_4$ are used for silicon dioxide, silicon nitride and silicon carbide deposition, respectively. The substrate holder temperature can be maintained at a highest temperature of 350° C. in this system to ensure a minimal amount of hydrogen incorporation in the film.

Figure 9:
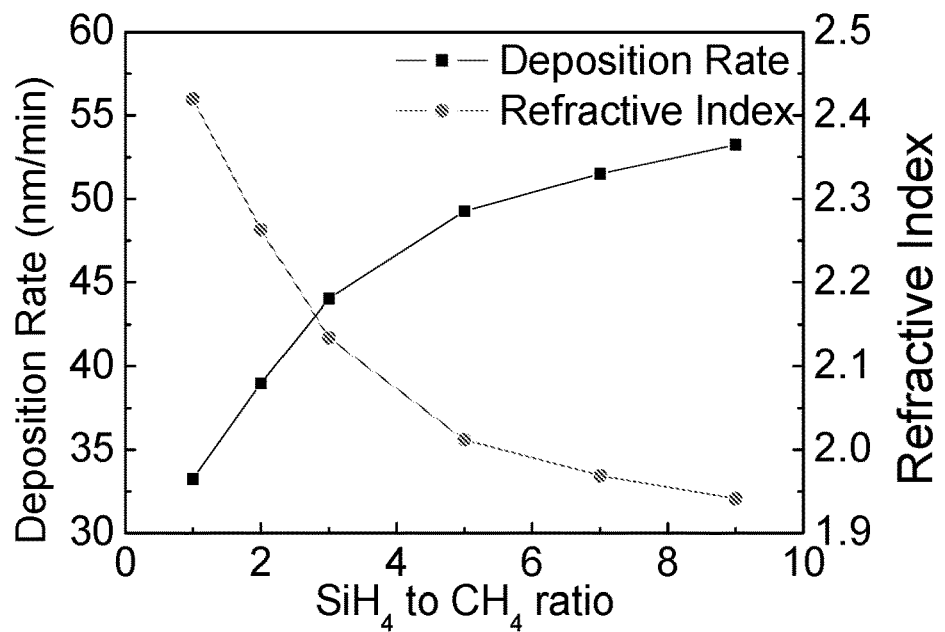
FIG. 9 is a graph illustrating the deposition rate and refractive index of PECVD SiC as a function of gas flow rate between $CH_4$ and $SiH_4$.

Experience gained from semiconductor device fabrication can be used to calibrate deposition conditions for silicon dioxide and silicon nitride. The deposition rate, refractive index, and stress of the SiC films is highly dependent on the deposition conditions, in terms of gas flow ratio between $CH_4$ and $SiH_4$, pressure, gas flow rate and rf power. Referring to FIG. 9, the deposition rate and refractive index can be dependent on the gas flow ratio between $CH_4$ and $SiH_4$. The graph of FIG. 9 assumes fixed rf power, pressure and temperature of 200 W, 1000 mTorr, and 350° C., respectively.

Silane ($SiH_4$) is flammable and has significant thermal expansion properties and therefore 2% $SiH_4$ in an inert gas is commonly employed in semiconductor device fabrication, and is suggested for use here. Due to the limited $SiH_4$ molecules available in 2% $SiH_4$, SiC deposition rates are restricted by the $SiH_4$ flow rate. Therefore, a gas flow controller with larger gas flow rates can be utilized to obtain SiC deposition rates >100 nm/min. In addition to deposition rates and refractive indexes, the residual stress of the SiC film can be measured to attain a low stress SiC film to improve SiC adhesion on the top of silicon dioxide.

To ensure good adhesion and abrasive resistance, processes including solvent boiling for degrease, ozone treatment for surface carbon contaminant removal, and short immersion in an acidic solution (e.g., a pH=2, to remove modifiers and fillers on the surface of the ceramic and expose silicon network for good binding between silicon network in the ceramic to PECVD silicon dioxide) can be incorporated into fabrication processes of the present invention.

Figure 10A:
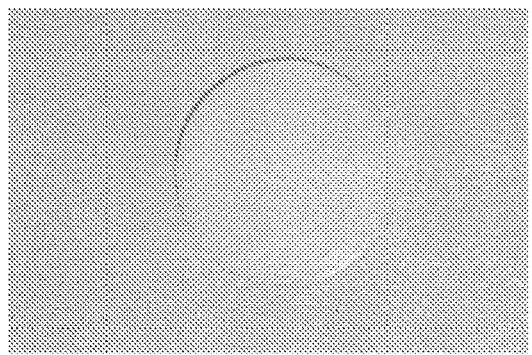
FIG. 10A is a photograph of a fluorapatite disk.
Figure 10B:
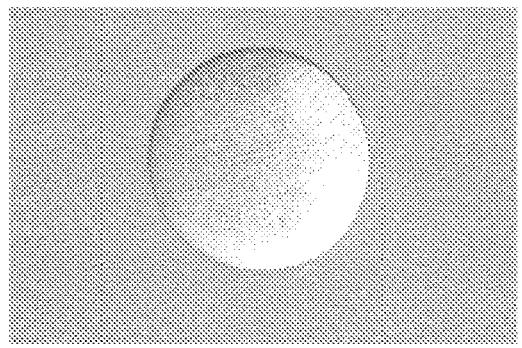
FIG. 10B is a photograph of a fluorapatite disk coated with 400 nm PECVD silicon nitride.
Figure 10C:
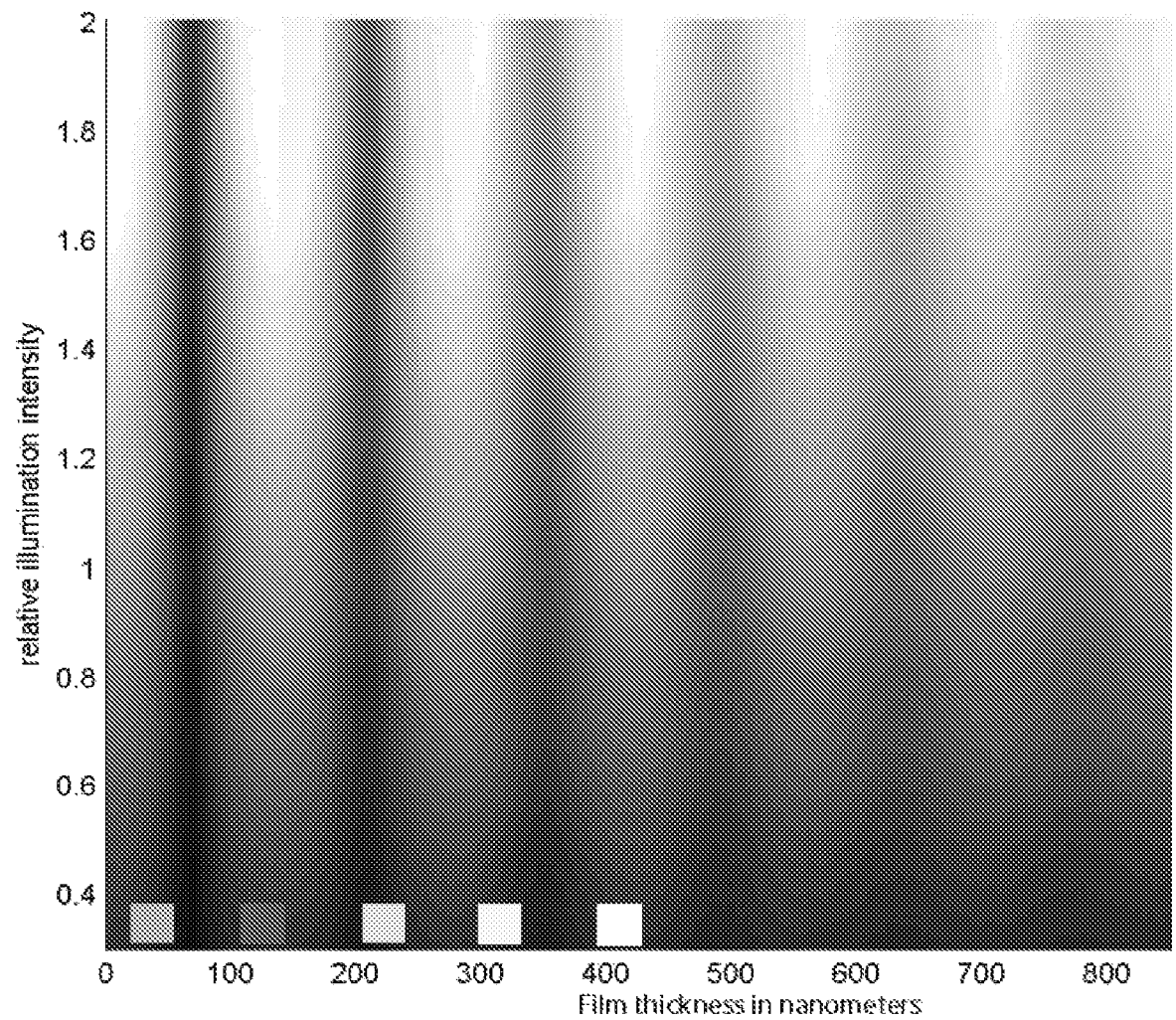
FIG. 10C is a graph illustrating the simulated color of a silicon substrate coated with different thicknesses of silicon nitride.

Due to a refractive index difference between the protective coating layer and veneering ceramics, a single protective layer deposited on the veneer can change the color of the veneer. Referring to FIGS. 10A and 10B, the color of 400-nm PECVD silicon nitride on a fluorapatite disk changed from a whitish appearance to a yellow-golden color. It is well known in semiconductor device fabrication that a variety of colors on silicon substrates can be achieved by depositing different thicknesses of silicon dioxide or silicon nitride on silicon substrates. FIG. 10C illustrates this phenomenon by showing the simulated color of a silicon substrate with different thicknesses of silicon nitride.

Figure 11A:
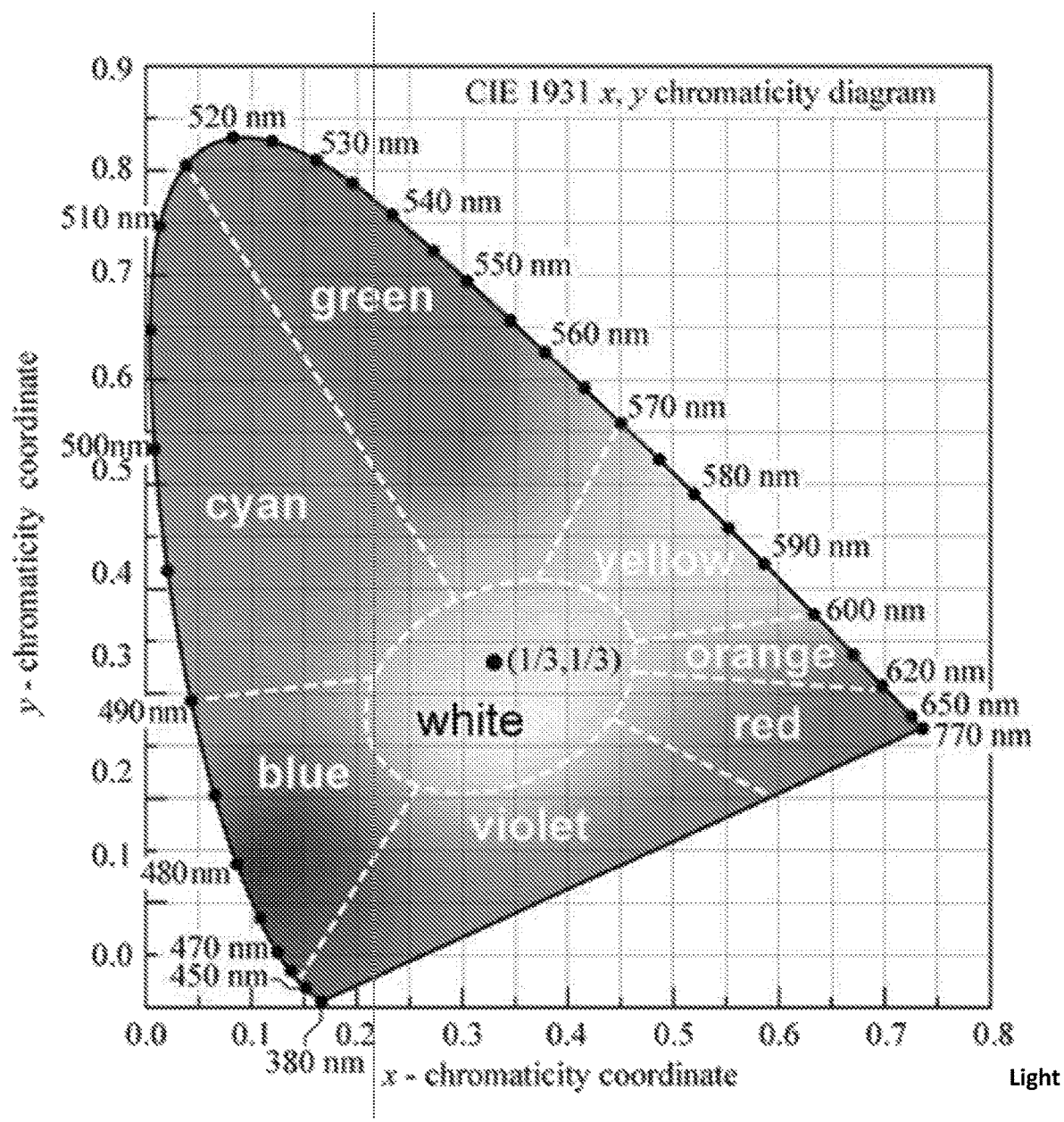
FIG. 11A is a CIE color chart.
Figure 11B:
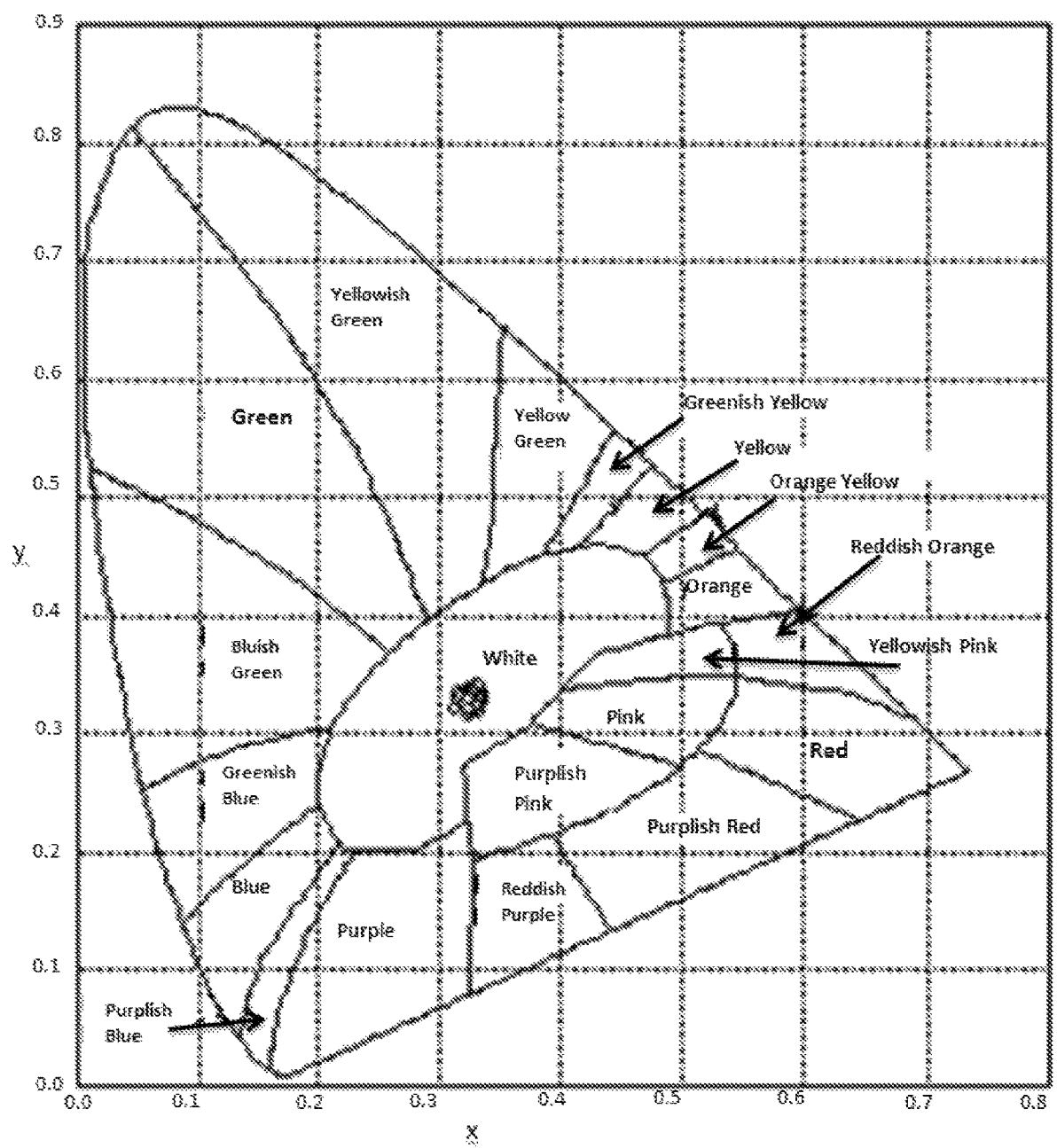
FIG. 11B illustrates simulated chromaticity coordinates of 4 to 12 layers of silicon dioxide and silicon nitride deposited on a fluorapatite disk.
Figure 12A:
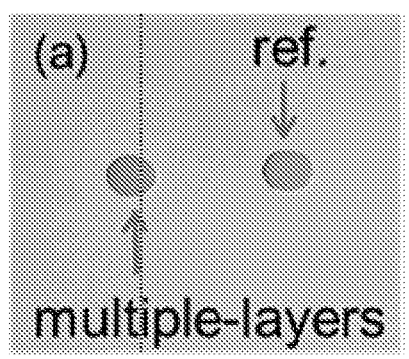
FIGS. 12A to 12D are photographs of a fluorapatite disks with and without 8 layers of silicon dioxide/silicon nitride coating taken at angle of: (A) 90°; (B) 60°; (C) 30°; and (D) 5-10°.
Figure 12B:
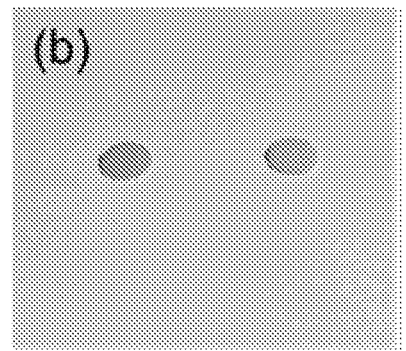
Figure 12C:
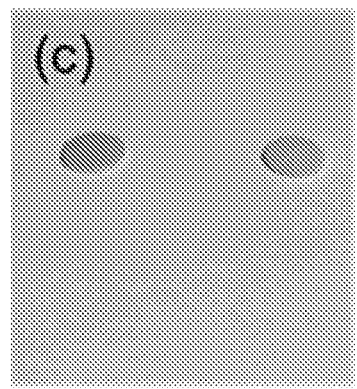
Figure 12D:
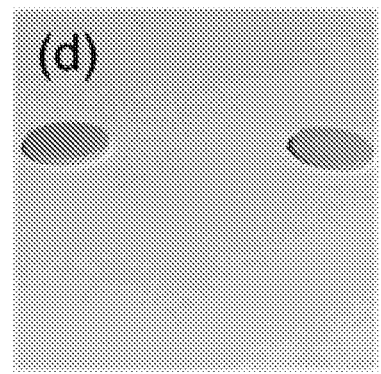
Figure 12E:
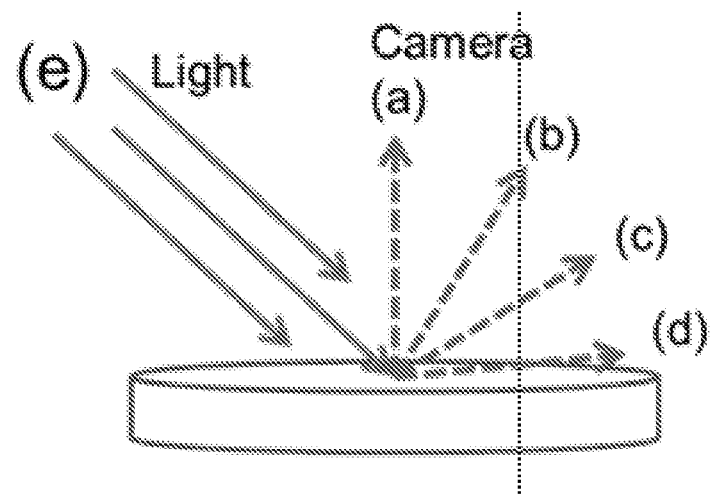
FIG. 12E is a schematic of the photographs of FIGS. 12A to 12D.

In order to maintain the original color of the fluorapatite disk, or any substrate for that matter, multiple layers of two different dielectric materials with different refractive indices can be used. Referring to FIG. 11A, the white color is located at the (x, y) chromaticity coordinate of (1/3, 1/3). Referring to FIG. 11B, the circles reside around (1/3, 1/3) representing the simulated (x, y) of 4 to 12 layers of the silicon dioxide and silicon nitride bilayer (a total of 8 to 24 layers) deposited on a fluorapatite disk. This would mean that the coated fluorapatite disk maintains its white color even when some of the silicon dioxide layers and silicon nitride layers are corroded.

FIG. 12 illustrates results of 8 layers of the silicon dioxide/silicon nitride bilayer (a total of 16 layers) deposited on a fluorapatite disk. There were very small differences of appearance observed from different angles of the disks between the coated and reference disk.

Embodiments of the subject invention include a dielectric coating or layers of dielectric coatings that can be added to the surface of a dental prosthetic to increase chemical durability and wear resistance and minimize surface roughness for decreased bacterial colonization. It is also feasible that one of the coating layers not be a dielectric material. Materials for dielectric coatings include $Al_2O_3$, SiCN, CN, $ZrO_2$, $SiN_x$, SiC, and $SiO_2$. Further examples of dielectric materials that can be applied include silicon oxynitride, silicon mono-oxide, boron nitride, silicon carbon nitride, silicon carbon oxide, metal oxides such as NaO, $Mg_2O$, $Al_2O_3$, and other refractory metal oxides, such as tungsten oxide, chromium oxide, molybdenum oxide, etc. There can be a single dielectric layer, multiple different dielectric layers, or two dielectric layers can be repeated alternately to make a stack of bilayers. The aim of using multiple dielectric layers and the layer material choice can be to achieve desired color, chemical resistance, hardness, adhesion, and wear characteristics. PECVD can be used to apply the dielectric layers and thicknesses for each layer can range from, for example, 5 nm to 500 nm.

FIGS. 13A to 13C are SEM micrographs with different magnifications showing the area around the edge of a ground fluoraptite disk coated with $SiC/SiO_2$, according to an embodiment of the present invention. In FIGS. 13A to 13C, a high quality bond can be seen between the SiC coating and the substrate. FIG. 13A shows an SEM micrograph that was taken at a 45° angle with 100× magnification, and the top SiC layer and the ground fluorapatite layer can be seen. FIG. 13B shows the top SiC layer, the ground SiC and the fluorapatite disk. However, the $SiO_2$ layer between the SiC and fluorapatite is too thin to be been seen. Even with 10,000× magnification, the $SiO_2$ layer cannot be seen, as shown in FIG. 13C. In FIGS. 13A to 13C, a high quality bond can be seen between an SiC coating and the substrate.

FIG. 14A is a graph of volume loss versus simulated chewing cycles in an experimental test of an embodiment of the present invention. FIG. 14B is a graph of maximum depth of material lost versus simulated chewing cycles in an experimental test of an embodiment of the present invention.

The subject invention includes, but is not limited to, the following exemplified embodiments.

Embodiment 1

A dental prosthetic restoration comprising a first dielectric coating.

Embodiment 2

The dental prosthetic restoration of embodiment 1, further comprising a second dielectric coating.

Embodiment 3

The dental prosthetic restoration of any of embodiments 1 to 2, wherein the first dielectric coating is SiC.

Embodiment 4

The dental prosthetic restoration of any of embodiments 2 to 3, wherein the first dielectric coating is SiC, the second dielectric layer is $SiO_2$, and the second dielectric layer is in direct contact with the dental prosthetic restoration.

Embodiment 5

The dental prosthetic restoration of any of embodiments 2 to 4, wherein the first dielectric coating and the second dielectric coating are alternately repeated to achieve a white color or the color of the dental prosthetic restoration.

Embodiment 6

The dental prosthetic restoration of any of embodiments 2 to 5, wherein the first dielectric coating and the second dielectric coating are alternately repeated with thicknesses from 5 nm to 500 nm (inclusive), each.

Embodiment 7

The dental prosthetic restoration of any of embodiments 2 to 6, wherein the first dielectric coating is on the occlusal surface of the dental prosthetic restoration and does not cover the inner surface of the dental prosthetic restoration.

Embodiment 8

The dental prosthetic restoration of any of embodiments 2 to 7, wherein the first dielectric coating and the second dielectric coating are each alternately layered three to thirteen times, for a total of six to twenty-six layers.

Embodiment 9

The dental prosthetic restoration of any of embodiments 1 to 8, further comprising between two and one-hundred additional dielectric coatings.

Embodiment 10

The dental prosthetic restoration of any of embodiments 1 to 9, wherein the dielectric coatings include one or more of $Al_2O_3$, $ZrO_2$, $SiN_x$, SiC, $SiO_2$, silicon oxynitride, silicon mono-oxide, boron nitride, silicon carbon nitride, silicon carbon oxide, metal oxides such as NaO, $Mg_2O$, $Al_2O_3$, and refractory metal oxides (such as tungsten oxide, chromium oxide, and molybdenum oxide).

Embodiment 11

The dental prosthetic restoration of any of embodiments 1 to 10, further comprising one or more polymer films before, between, or after the dielectric coatings.

Embodiment 101

A method of improving a dental prosthetic restoration, comprising:
providing the dental prosthetic restoration;
coating the dental prosthetic restoration with a first dielectric material.

Embodiment 102

The method of embodiment 101, further comprising, coating the dental prosthetic restoration with a second dielectric material.

Embodiment 103

The method of any of embodiments 101 to 102, wherein the first dielectric material is SiC.

Embodiment 104

The method of any of embodiments 101 to 103, wherein the second dielectric material is $SiO_2$.

Embodiment 105

The method of any of embodiments 101 to 104, wherein the first dielectric material and the second dielectric material are one or more of $Al_2O_3$, $ZrO_2$, $SiN_x$, SiC, and $SiO_2$.

Embodiment 106

The method of any of embodiments 101 to 105, wherein the first dielectric material and the second dielectric material are alternately layered three to twelve times, for a total of six to twenty-four layers.

Embodiment 107

The method of any of embodiments 101 to 106, wherein one or more of the first dielectric material and the second dielectric material are applied using a plasma enhanced chemical vapor deposition (PECVD) process.

Embodiment 108

The method of any of embodiments 101 to 107, wherein an outer surface of the dental prosthetic restoration is a glass-based veneering ceramic.

Embodiment 109

The method of any of embodiments 101 to 108, wherein the first dielectric material is $SiN_x$ and the second dielectric material is $Al_2O_3$.

Embodiment 201

A method for testing dental prosthetic restorations comprising:
providing a basic solution;
providing an acidic solution;
immersing a test device in both the basic solution and the acidic solution; and
evaluating corrosion and damage of the test device.

Embodiment 202

The method of embodiment 201, further comprising:
providing a neutral solution;
and immersing the test device in the neutral solution.

Embodiment 203

The method of any of embodiments 201 to 202, wherein the basic solution is from pH 8.5 to 10.5, the acidic solution is from pH 1.5 to 2.5, and the neutral solution is from pH 6.5 to 7.5.

Embodiment 204

The method of any of embodiments 201 to 203 wherein the test device cycles from the basic solution, to the neutral solution, to the acidic solution.

Embodiment 205

The method of any of embodiments 201 to 204, wherein the test device cycles from the basic solution, to the acidic solution, to the neutral solution.

Embodiment 206

The method of any of embodiments 201 to 205, wherein the test device is a dental prosthetic restoration.

Embodiment 207

The method of any of embodiments 201 to 206, wherein the test device is an object used to emulate a dental prosthetic restoration.

Embodiment 208

The method of any of embodiments 201 to 207, wherein the cycling from the basic solution, to the neutral solution, to the acidic solution is completed between two and ten times for all three solutions.

Embodiment 209

The method of any of embodiments 201 to 208, wherein a time spent in each solution ranges from 6 to 96 hours.

Embodiment 210

The method of any of embodiments 201 to 209, wherein a time spent in each solution ranges from 1 to 6 hours.

Embodiment 211

The method of any of embodiments 201 to 210, wherein a time spent in each solution ranges from 10 minutes to 1 hour.

Embodiment 212

The method of any of embodiments 201 to 211, wherein a time spent in each solution ranges from 1 to 10 minutes.

Embodiment 213

The method of any of embodiments 201 to 212, wherein the test device cycles from the basic solution to the acidic solution.

Embodiment 214

The method of any of embodiments 201 to 213, wherein the test device cycles from the basic solution to the acidic solution (or vice versa).

Embodiment 215

The method of any of embodiments 201 to 213, wherein a condition of the test device is measured intrinsically (e.g., by physical roughness, porosity, tensile strength, surface analysis such as sem microscopy, etc).

Embodiment 216

The method of any of embodiments 201 to 214, wherein a condition of the test device is measured extrinsically (e.g., by measuring changes in pH or dissolved materials in the acidic, basic, or neutral solutions).

Embodiment 301

A dielectric coating layer that includes a single layer or multiple layers of dielectric materials, each layer including silicon dioxide, silicon mono-oxide, silicon nitride, silicon oxynitride, boron nitride, silicon carbide, silicon carbon nitride, silicon carbon oxide, aluminum oxide, zirconium oxide, other metal oxides, or a combination thereof.

Embodiment 401

A wet chemical cycling system, which introduces different pH values, solution temperatures (which can range from room temperature, e.g., 25° C., to 250° C.), cycling sequences and cycling time periods, as well as collects solution samples, for evaluating the resistance of tested materials in different pH solutions.

Embodiment 402

The method of embodiment 31 with the inclusion of abrasion testing using a chewing simulator at varying intervals in between the different pH immersions ranging from a load of 10N to 250N and cycles of 5,000 to 300,000.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 4:
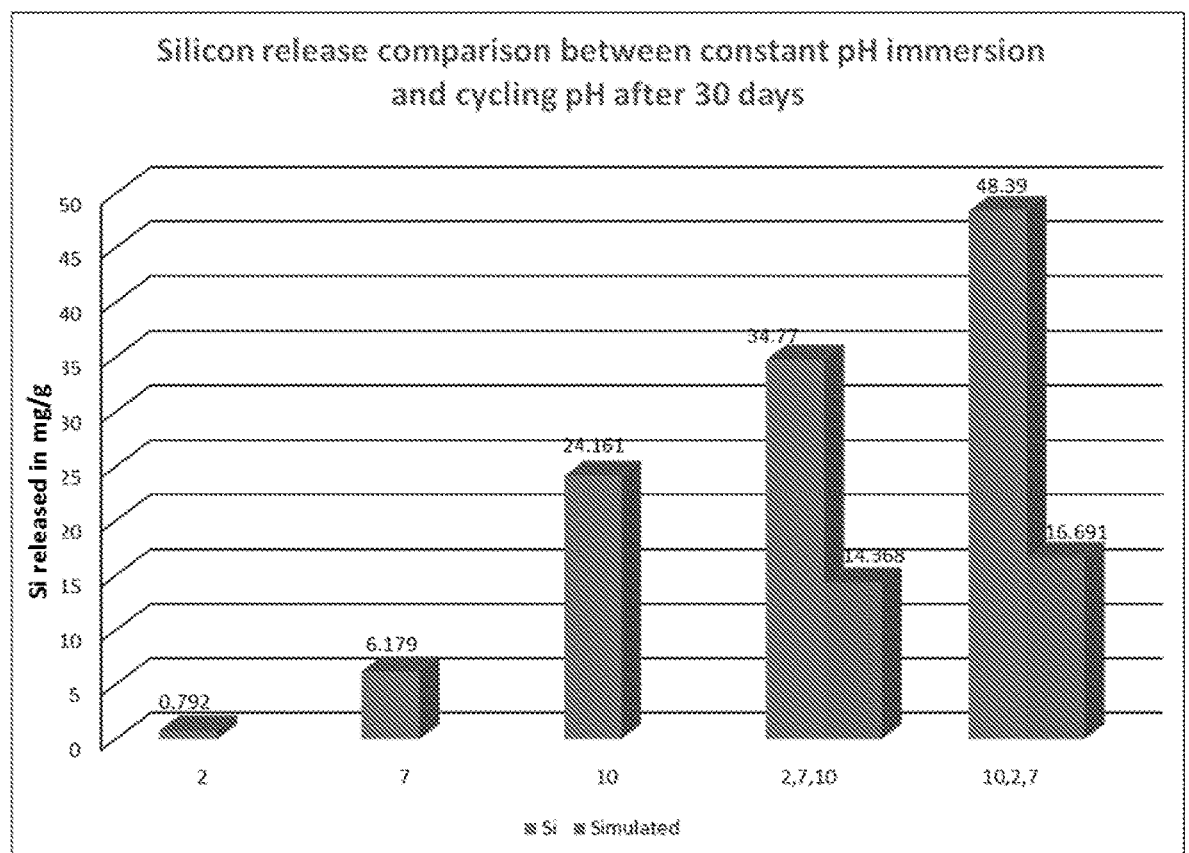
FIG. 4 is a graph that displays silicon (Si) release rates between constant immersion and pH cycling immersion.

For a cycling pH oral prosthetic restoration testing method, the amount of silicon (which is the main building block of glass-ceramics) released was measured for a total of 30 days by alternating between pH 2, 7 and 10. The ceramic was immersed in each solution for 3 days and moved to the next solution in the pattern for a total of ten cycles (for a total of four 3-day cycles of pH 2, three 3-day cycles of pH 7, and three 3-day cycles at pH 7). The Si released at 30-days for alternating pH levels of 10, 2, 7 for 30 days was three times higher than that for the constant immersion at pH 10 (FIG. 4). Additionally, 30-day data for alternating pH levels of 2, 7, and 10 demonstrated Si release that was 44 times higher than the Si released for the constant immersion at pH 2.

In order to demonstrate how the cycling of pH increases the amount of Si released, FIG. 4 has a simulated release rate that has been calculated using data generated from immersions at constant pH. For example, with alternating pH levels of 2, 7, 10 for 30 days, four constant pH 2 cycles, three constant pH 7 cycles, and three constant pH 10 cycles were added. This simulated release amount was 14.37 mg/g, which is far below the observed release rates produced by the cycling methodology. This data demonstrates that cycling pHs to different levels magnifies the release rate of silicon relative to maintaining constant pHs levels.

Example 2

The method of Example 1 was repeated, but as part of the testing method, abrasive or chewing steps were inserted. Ninety coated samples with different surface treatments were subjected to 30 day immersion in pH solutions (2, 7 and 10) and 5,000 cycles of wear and adhesion testing were conducted in a chewing simulator after every 3 days, for a total of 25,000 cycles of uniform circular motion at a revolving speed of 90 r/min and r=0.5 mm. For analysis, the coated samples can be divided into three groups, each subject to a different pH sequence. One sample can be retrieved for each solution and pH cycle for XPS (X-ray photoelectron spectroscopy) and SEM (scanning electron microscope) analysis and all solutions for each cycle can be retrieved after each cycle for ICP analysis.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

Aksoy G, Polat H, Polat M, Coskun G (2006). Effect of various treatment and glazing (coating) techniques on the roughness and wettability of ceramic dental restorative surfaces. Colloids Surf B Biointerfaces 53(2):254-259.

Al-Marzok M I, Al-Azzawi H J (2009). The effect of the surface roughness of porcelain on the adhesion of oral *Streptococcus mutans*. J Contemp Dent Pract 10(6):E017-024.

Bartlett D W, Fares J, Shirodaria S, Chiu K, Ahmad N, Sherriff M (2011). The association of tooth wear, diet and dietary habits in adults aged 18-30 years old. J Dent 39(12):811-816.

Butler C J, Masri R, Driscoll C F, Thompson G A, Runyan D A, Anthony von Fraunhofer J (2004). Effect of fluoride and 10% carbamide peroxide on the surface roughness of low-fusing and ultra low-fusing porcelain. J Prosthet Dent 92(2):179-183.

Ccahuana V Z, Ozcan M, Mesquita A M, Nishioka R S, Kimpara E T, Bottino M A (2010). Surface degradation of glass ceramics after exposure to acidulated phosphate fluoride. J Appl Oral Sci 18(2):155-165.

Creugers N H, Kayser A F, van't Hof M A (1994). A meta-analysis of durability data on conventional fixed bridges. Community Dent Oral Epidemiol 22(6):448-452.

Drummond J L, Novickas D, Lenke J W (1991). Physiological aging of an all-ceramic restorative material. Dent Mater 7(2):133-137.

Esquivel-Upshaw J, Rose W, Oliveira E, Yang M, Clark A E, Anusavice K (2013). Randomized, controlled clinical trial of bilayer ceramic and metal-ceramic crown performance. J Prosthodont 22(3):166-173.

Esquivel-Upshaw J F, Chai J, Sansano S, Shonberg D (2001). Resistance to staining, flexural strength, and chemical solubility of core porcelains for all-ceramic crowns. The International journal of prosthodontics 14(3): 284-288.

Esquivel-Upshaw J F, Young H, Jones J, Yang M, Anusavice K J (2006). In vivo wear of enamel by a lithia disilicate-based core ceramic used for posterior fixed partial dentures: first-year results. The International journal of prosthodontics 19(4):391-396.

Esquivel-Upshaw J F, Dieng F Y, Clark A E, Neal D, Anusavice K J (2013). Surface Degradation of Dental Ceramics as a Function of Environmental pH. J Dent Res 92(5):467-471.

Esquivel-Upshaw J R, W. Oliveira, E. Yang, M K. Clark, A E. Anusavice, K J. (2012). Randomized, controlled clinical trial of bilayer-ceramic and metal-ceramic crown performance. J Prosthodont Fischer H, Schafer M, Marx R (2003). Effect of surface roughness on flexural strength of veneer ceramics. J Dent Res 82(12):972-975.

Flannery A F, Mourlas N J, Storment C W, Tsai S, Tan S H, Heck J et al. (1998). PECVD silicon carbide as a chemically resistant material for micromachined transducers. Sensors and Actuators A: Physical 70(1-2):48-55.

Haixia Z, Hui G, Zhe C, Guobing Z, Zhihong L (2007). Application of PECVD SiC in glass micromachining. Journal of Micromechanics and Microengineering 17(4): 775.

Heintze S D, Rousson V (2010). Survival of zirconia- and metal-supported fixed dental prostheses: a systematic review. Int J Prosthodont 23(6):493-502.

Herrmann M, Schilm J, Michael G, Meinhardt J, Flegler R (2003). Corrosion of silicon nitride materials in acidic and basic solutions and under hydrothermal conditions. J Eur Cer Soc 23(585-594.

Herrmann M (2013). Corrosion of Silicon Nitride Materials in Aqueous Solutions. J Am Ceram Soc 96(10):3009-3022.

Junpoom P, Kukiattrakoon B, Hengtrakool C (2010). Surface characteristic changes of dental ceramics after cyclic immersion in acidic agents and titratable acidity. Eur J Prosthodont Restor Dent 18(4):177-184.

Kukiattrakoon B, Junpoom P, Hengtrakool C (2009). Vicker's microhardness and energy dispersive x-ray analysis of fluorapatite-leucite and fluorapatite ceramics cyclically immersed in acidic agents. J Oral Sci 51(3):443-450.

Kukiattrakoon B, Hengtrakool C, Kedjarune-Leggat U (2010a). The effect of acidic agents on surface ion leaching and surface characteristics of dental porcelains. J Prosthet Dent 103(3):148-162.

Kukiattrakoon B, Hengtrakool C, Kedjarune-Leggat U (2010b). Degradability of fluorapatite-leucite ceramics in naturally acidic agents. Dent Mater J 29(5):502-511.

Kukiattrakoon B, Hengtrakool C, Kedjarune-Leggat U (2010c). Chemical durability and microhardness of dental ceramics immersed in acidic agents. Acta Odontol Scand 68(1):1-10.

Kukiattrakoon B, Hengtrakool C, Kedjarune-Leggat U (2011). Effect of acidic agents on surface roughness of dental ceramics. Dent Res J (Isfahan) 8(1):6-15.

Milleding P, Gerdes S, Holmberg K, Karlsson S (1999). Surface energy of non-corroded and corroded dental ceramic materials before and after contact with salivary proteins. Eur J Oral Sci 107(5):384-392.

Miyazaki T, Nakamura T, Matsumura H, Ban S, Kobayashi T (2013). Current status of zirconia restoration. Journal of Prosthodontic Research 57(4):236-261.

Pinto M M, Cesar P F, Rosa V, Yoshimura H N (2008). Influence of pH on slow crack growth of dental porcelains. Dent Mater 24(6):814-823.

Preis V, Behr M, Handel G, Schneider-Feyrer S, Hahnel S, Rosentritt M (2012). Wear performance of dental ceramics after grinding and polishing treatments. J Mech Behav Biomed Mater 10(13-22.

Raigrodski A J, Chiche G J (2001). The safety and efficacy of anterior ceramic fixed partial dentures: A review of the literature. J Prosthet Dent 86(5):520-525.

Rosenstiel S F, Gupta P K, Van Der Sluys R A, Zimmerman M H (1993). Strength of a dental glass-ceramic after surface coating. Dent Mater 9(274-279.

Sailer I, Pjetursson B E, Zwahlen M, Hammerle C H (2007). A systematic review of the survival and complication rates of all-ceramic and metal-ceramic reconstructions after an observation period of at least 3 years. Part I I: Fixed dental prostheses. Clin Oral Implants Res 18 Suppl 3(86-96.

Salido M P, Martinez-Rus F, del Rio F, Pradies G, Ozcan M, Suarez M J (2012). Prospective clinical study of zirconia-based posterior four-unit fixed dental prostheses: four-year follow-up. Int J Prosthodont 25(4):403-409.

Scurria M S, Bader J D, Shugars D A (1998). Meta-analysis of fixed partial denture survival: prostheses and abutments. J Prosthet Dent 79(4):459-464.

U.S. Pat. No. 3,422,535

What is claimed is:

1. A dental prosthetic restoration, consisting of:
    a first dielectric layer disposed on a ceramic substrate, wherein the first dielectric layer consists of silicon oxide, silicon dioxide, silicon oxynitride, or any combination thereof, and has a thickness of 5 nm to 40 nm; and
    a second dielectric layer disposed on the first dielectric layer, wherein the second dielectric layer consists of silicon carbide, silicon nitride, or silicon carbon nitride.

2. The dental prosthetic restoration of claim 1, wherein the first dielectric layer consists of silicon dioxide.

3. The dental prosthetic restoration of claim 1, wherein the first dielectric layer has a thickness from 5 nm to 40 nm and the second dielectric layer has a thickness from 100 nm to 10,000 nm.

4. The dental prosthetic restoration of claim 1, wherein the first dielectric layer is on an occlusal surface of the dental prosthetic restoration.

5. The dental prosthetic restoration of claim 1, wherein the first dielectric layer or the second dielectric layer are applied using a plasma spray or plasma enhanced chemical vapor deposition.

6. The dental prosthetic restoration of claim 1, wherein the ceramic substrate consists of a glass ceramic substrate.

7. The dental prosthetic restoration of claim 1, wherein the second dielectric layer has a thickness of 100 nm to 10,000 nm.

8. The dental prosthetic restoration of claim 1, wherein the second dielectric layer consists of silicon carbide (SiC).

9. A dental prosthetic restoration, consisting of:
a ceramic substrate;
a first dielectric layer disposed on the ceramic substrate, wherein the first dielectric layer consists of silicon dioxide ($SiO_2$) and has a thickness of 5 nm to 40 nm; and
a second dielectric layer disposed on the first dielectric layer, wherein the second dielectric layer consists of silicon carbide (SiC) and has a thickness of 100 nm to 10,000 nm.

\* \* \* \* \*